United States Patent
Shmulewitz et al.

[11] Patent Number: 6,027,457
[45] Date of Patent: Feb. 22, 2000

[54] APPARATUS AND METHOD FOR SECURING TISSUE DURING ULTRASOUND EXAMINATION AND BIOPSY

[75] Inventors: Ascher Shmulewitz, Mercer Island; Peter A. Crosby, Bellevue, both of Wash.

[73] Assignee: United States Surgical Corporation, Norwalk, Conn.

[21] Appl. No.: 09/099,490

[22] Filed: Jun. 18, 1998

[51] Int. Cl.[7] .............................. A61B 8/00; A61B 10/00
[52] U.S. Cl. ......................... 600/562; 600/437; 600/461
[58] Field of Search .................................. 600/437, 442, 600/445, 464, 562, 567, 461

[56] References Cited

U.S. PATENT DOCUMENTS

| | | |
|---|---|---|
| Re. 30,397 | 9/1980 | King . |
| 2,707,662 | 5/1955 | Goldfield et al. . |
| 3,165,630 | 1/1965 | Bielat et al. . |
| 3,420,097 | 1/1969 | Battermann et al. . |
| 3,480,002 | 11/1969 | Flaherty et al. . |
| 3,556,081 | 1/1971 | Jones . |
| 3,589,361 | 6/1971 | Loper . |
| 3,609,355 | 9/1971 | Kwarzen . |
| 3,765,403 | 10/1973 | Brenden . |
| 3,921,442 | 11/1975 | Soloway . |
| 3,939,696 | 2/1976 | Kossoff . |
| 3,963,933 | 6/1976 | Henkes, Jr. . |
| 3,971,950 | 7/1976 | Evans et al. . |
| 3,973,126 | 8/1976 | Redington et al. . |
| 3,990,300 | 11/1976 | Kossoff . |
| 3,991,316 | 11/1976 | Schmidt et al. . |
| 4,021,771 | 5/1977 | Collins et al. . |
| 4,051,380 | 9/1977 | Lasky . |
| 4,058,114 | 11/1977 | Soldner . |
| 4,094,306 | 6/1978 | Kossoff . |
| 4,099,880 | 7/1978 | Kano . |
| 4,167,180 | 9/1979 | Kossoff . |
| 4,206,763 | 6/1980 | Pederson . |

(List continued on next page.)

FOREIGN PATENT DOCUMENTS

| | | |
|---|---|---|
| 105 812 | 4/1984 | European Pat. Off. . |
| 483 005 | 4/1992 | European Pat. Off. . |
| 581 704 | 2/1994 | European Pat. Off. . |
| 70 23 909 | of 0000 | Germany . |
| 23 35 576 | 1/1975 | Germany . |
| 32 26 976 | 7/1981 | Germany . |
| 32 22 053 | 12/1983 | Germany . |
| 32 27 624 | 1/1984 | Germany . |
| 34 05 537 | 8/1985 | Germany . |
| 34 47 444 | 7/1986 | Germany . |
| 26 3228 | 12/1988 | Germany . |
| 38 29 259 | 3/1989 | Germany . |
| 40 37 387 | 5/1992 | Germany . |
| 896 539 | 4/1980 | U.S.S.R. . |
| 2 094 590 | 9/1982 | United Kingdom . |
| 83/02053 | 6/1983 | WIPO . |
| 88/08272 | 11/1988 | WIPO . |
| 89/11248 | 11/1989 | WIPO . |
| 94/21189 | 9/1994 | WIPO . |
| 95/11627 | 5/1995 | WIPO . |

OTHER PUBLICATIONS

Magnusson, A., "New Stereotactic Instrument Facilitates Computer Tomographically Guided Punctio", Läkartidningen, vol. 86, No. 21, pp. 1885–1886, 1888 (1988).

(List continued on next page.)

*Primary Examiner*—Marvin M. Lateef
*Assistant Examiner*—Ali M. Imam

[57] ABSTRACT

An ultrasound imaging and biopsy system is provided in which an upper compression member of the system includes a thin, flexible, sterile and disposable membrane that compresses the tissue and permits a biopsy instrument to be readily inserted therethrough. In a preferred embodiment, a table is provided that houses an ultrasound scanning system beneath a sonolucent window forming a lower compression surface. Methods of using the system to perform real-time image-guided biopsy of tissue disposed on the window are also provided.

20 Claims, 4 Drawing Sheets

U.S. PATENT DOCUMENTS

| | | |
|---|---|---|
| 4,249,541 | 2/1981 | Pratt . |
| 4,285,010 | 8/1981 | Wilcox . |
| 4,343,799 | 8/1982 | Heckler . |
| 4,347,850 | 9/1982 | Kelly-Fry et al. . |
| 4,363,326 | 12/1982 | Kopel . |
| 4,369,284 | 1/1983 | Chen . |
| 4,402,324 | 9/1983 | Lindgren et al. . |
| 4,433,690 | 2/1984 | Green et al. . |
| 4,434,799 | 3/1984 | Taenzer . |
| 4,455,872 | 6/1984 | Kossoff et al. . |
| 4,465,069 | 8/1984 | Barbier et al. . |
| 4,469,106 | 9/1984 | Harui . |
| 4,485,819 | 12/1984 | Igl . |
| 4,497,325 | 2/1985 | Wedel . |
| 4,501,278 | 2/1985 | Yamaguchi et al. . |
| 4,527,569 | 7/1985 | Kolb . |
| 4,541,436 | 9/1985 | Hassler et al. . |
| 4,545,385 | 10/1985 | Pirschel . |
| 4,573,180 | 2/1986 | Summ . |
| 4,579,123 | 4/1986 | Chen et al. . |
| 4,583,538 | 4/1986 | Onik et al. . |
| 4,592,352 | 6/1986 | Patil . |
| 4,599,738 | 7/1986 | Panetta et al. . |
| 4,608,989 | 9/1986 | Drue . |
| 4,613,122 | 9/1986 | Manabe . |
| 4,613,982 | 9/1986 | Dornheim et al. . |
| 4,618,213 | 10/1986 | Chen . |
| 4,618,973 | 10/1986 | Lasky . |
| 4,625,555 | 12/1986 | Fujii . |
| 4,671,292 | 6/1987 | Matzuk . |
| 4,681,103 | 7/1987 | Boner et al. . |
| 4,686,997 | 8/1987 | Oloff et al. . |
| 4,722,346 | 2/1988 | Chen . |
| 4,727,565 | 2/1988 | Ericson . |
| 4,733,661 | 3/1988 | Palestrant . |
| 4,735,215 | 4/1988 | Goto et al. . |
| 4,750,487 | 6/1988 | Zanetti . |
| 4,774,961 | 10/1988 | Carr . |
| 4,784,134 | 11/1988 | Arana . |
| 4,791,934 | 12/1988 | Brunnett . |
| 4,821,727 | 4/1989 | Levene et al. . |
| 4,844,080 | 7/1989 | Frass et al. . |
| 4,862,893 | 9/1989 | Martinelli . |
| 4,869,247 | 9/1989 | Howard, III et al. . |
| 4,875,478 | 10/1989 | Chen . |
| 4,890,311 | 12/1989 | Saffer . |
| 4,898,178 | 2/1990 | Wedel . |
| 4,899,756 | 2/1990 | Sonek . |
| 4,911,173 | 3/1990 | Terwilliger . |
| 4,930,143 | 5/1990 | Lundgren et al. . |
| 4,940,061 | 7/1990 | Terwilliger et al. . |
| 4,944,308 | 7/1990 | Akerfeldt . |
| 4,953,558 | 9/1990 | Akerfeldt . |
| 4,962,515 | 10/1990 | Kopans . |
| 4,962,752 | 10/1990 | Reichenberger et al. . |
| 4,966,152 | 10/1990 | Gäng et al. . |
| 4,981,142 | 1/1991 | Dachman . |
| 5,003,979 | 4/1991 | Merickel et al. . |
| 5,007,428 | 4/1991 | Watmough . |
| 5,029,193 | 7/1991 | Saffer . |
| 5,056,523 | 10/1991 | Hotchkiss, Jr. et al. . |
| 5,078,142 | 1/1992 | Siczek et al. . |
| 5,078,149 | 1/1992 | Katsumata et al. . |
| 5,083,305 | 1/1992 | Tirelli et al. . |
| 5,095,910 | 3/1992 | Powers . |
| 5,099,503 | 3/1992 | Strömmer . |
| 5,107,843 | 4/1992 | Aarnio et al. . |
| 5,113,420 | 5/1992 | Davis, Jr. et al. . |
| 5,158,088 | 10/1992 | Nelson et al. . |
| 5,199,056 | 3/1993 | Darrah . |
| 5,205,297 | 4/1993 | Montecalvo et al. . |
| 5,219,351 | 6/1993 | Teubner et al. . |
| 5,260,871 | 11/1993 | Goldberg . |
| 5,262,468 | 11/1993 | Chen . |
| 5,273,435 | 12/1993 | Jacobson . |
| 5,280,427 | 1/1994 | Magnusson et al. . |
| 5,305,365 | 4/1994 | Coe . |
| 5,318,028 | 6/1994 | Mitchell et al. . |
| 5,361,768 | 11/1994 | Webler et al. . |
| 5,379,769 | 1/1995 | Ito et al. . |
| 5,386,447 | 1/1995 | Siczek . |
| 5,396,897 | 3/1995 | Jain et al. . |
| 5,411,026 | 5/1995 | Carol . |
| 5,415,169 | 5/1995 | Siczek et al. . |
| 5,426,685 | 6/1995 | Pellegrino et al. . |
| 5,433,202 | 7/1995 | Mitchell et al. . |
| 5,447,154 | 9/1995 | Cinquin et al. . |
| 5,450,851 | 9/1995 | Hancock . |
| 5,474,072 | 12/1995 | Shmulewitz . |
| 5,479,927 | 1/1996 | Shmulewitz . |
| 5,487,387 | 1/1996 | Trahey et al. . |
| 5,488,952 | 2/1996 | Schoolman . |
| 5,499,989 | 3/1996 | LaBash . |
| 5,506,877 | 4/1996 | Niklason et al. . |
| 5,522,787 | 6/1996 | Evans . |
| 5,524,636 | 6/1996 | Sarvazyan et al. . |
| 5,594,769 | 1/1997 | Pellegrino et al. . |
| 5,595,177 | 1/1997 | Mena et al. . |
| 5,603,326 | 2/1997 | Richter . |
| 5,609,152 | 3/1997 | Pellegrino et al. . |
| 5,640,956 | 6/1997 | Getzinger et al. . |
| 5,660,185 | 8/1997 | Shmulewitz et al. . |
| 5,664,573 | 9/1997 | Shmulewitz et al. . |

OTHER PUBLICATIONS

Gardineer et al., "Video–photographic System for Rapid Inexpensive Unit Recording and Flexible Replay of Real–time Ultrasonic Imaging of the Breast", SPIE, vol. 273, Appln. of Optical Instrumentation in Medicine IX, pp. 343–347 (1981).

Bruno D. Fornage, MD et al., Breast Masses: US–Guided Fine–Needle Aspiration Biopsy[1], Radiology, 162:409–414 (1987).

B.D. Fornage, MD et al., "Ultrasound–Guided Needle Biopsy of the Breast and Other Interventional Procedures", vol. 30, No. 1, pp. 167–185 (Jan. 1992).

Darla Haight et al., "Radiologists Spread Their Wings: A Look at the Possibilities in STereotactic Breast Biopsy", Admin. Rad. J., pp. 87–89 (Nov. 1987).

E. Azavedo et al., "Stereotactic Fine–Needle Biopsy in 2594 Mammographically Detected Non–Palable Lesions", The Lancet, pp. 1033–1036 (May 1989).

Eva Rubin, MD, "Breast Cancer in the 90's", Applied Radiology, pp. 23–26 (Mar. 1993).

Ellen B. Mendelson, MD, "Ultrasound Secures Place in Breast Ca Management", Diagnostic Imaging, pp. 120–129 (Apr. 1991).

Ferris H. Hall, MD, "Mammographic Second Opinions Prior to Biopsy of Nonpalpable Beast Lesions", Arch Surg, vol. 125, pp. 298–299 (Mar. 1990).

Gunilla Svane, MD., "Stereotactic Needle Biopsy", Dept. pf Dianostic Radioloyg at the Karolinska Hospital, Stockholm, Sweden (1987).

Gillian Newstead, MD., "When and When Not to Biopsy the Breast", Diagnostic Imaging, pp. 111–116, (Mar. 1993).

Ingvar Andersson, MD, "Medical Radiography and Photography", vol. 62, No. 2, pp. 2–41 (1986).

Jan Bolmgren, et al., "Stereotaxic Instrument for Needle Biopsy of the Mamma", (Sweden) J. Radiology, 129:121–125 (Jul. 1977).

Kambiz Dowlatsashahi, MD, Breast Care: "The Needle Replaces The Knife" (Exploring Sterotatic Guided Needle Biopsy), Admin. Radiology, pp. 28–31 (Jun. 1989).

K. Dowlatshahi, MD, "Palable Breast Tumors: Diagnosis with Stereotaxic Localization and Fine–needle Aspiration", Radiology 170, no. 2, pp. 427–433 (Feb. 1989).

Ralph Mösges et al., "Multimodal Information for Computer–Integrated Surgery", Mösges & Lavallée: Multimodal Information for CIS/Data Acquisition & Segmentation, pp. 5–19.

Rachel F. Brem, MD et al., "Template–guided Breast US[1]", Radiology 184:872–874 (Sep. 1992).

Steve H. Parker, MD et al., "Percutaneous Large–Core Breast Biopsy: A Multi–institutional Study[1]", Radiology vol. 193, No. 2, pp. 359–364 (Nov. 1994).

S.H. Parker, MD et al., "Large–Core Breast Biopsy Offers Reliable", Diagnostic Imaging, 8 pages (Oct. 1990).

S.H. Parker, MD et al., "US–guided Automated Large–Core Breast Biopsy[1]", Radiology, 187:507–511 (May 1993).

P.N.T. Wells et al., "Tumor detection by ultrasonic Doppler blood–flow signals", Ultrasonics, pp. 231–232 (Sep. 1977).

Valerie P. Jackson, MD, "The Role of US in Breast Imaging[1]", Radiology 177:305–311 RSNA (Nov. 1990).

W. Phil Evans, MD et al., "Needle Localization and Fine–Needle Aspiration Biopsy of Nonpalpable Breast Lesions with use of Standard and Stereotactic Equipment", Radiology, 173:53–56 (1989).

William F. Conway, MD et al., "Occult Breast Masses: Use of a Mammographic Localizing Grid for US Evaluation[1]", Radiology, 181:143–146 (1991).

APPARATUS AND METHOD FOR SECURING TISSUE DURING ULTRASOUND EXAMINATION AND BIOPSY

BACKGROUND

1. Technical Field

The present disclosure relates to methods and apparatus for conducting ultrasound examination and biopsy of biological tissue. More specifically, the present disclosure provides apparatus and methods for securing biological tissue while permitting ready access to perform a biopsy guided by a real-time ultrasound image of the tissue.

2. Background of Related Art

A number of previously known devices have been developed to permit image-guided biopsy of biological tissue. Such systems recognize that to perform an effective biopsy less-invasively, the clinician must be able to guide the biopsy instrument to a suspected lesion with high accuracy. Without visual confirmation that the biopsy instrument has indeed excised a portion of the suspected lesion, the risk exists that the biopsy may have excised only a portion of healthy tissue, thereby leading to misdiagnosis.

Many of the previously known systems have been unsuitable for performing real-time, image guided biopsy. Such systems, as described, for example, in U.S. Pat. No. 3,765,403 to Brenden and U.S. Pat. No. 3,963,933 to Henkes, Jr., require the patient to lay prone and insert her breast into a water-filled bath. There is no capability in such systems to position and insert a biopsy instrument into the breast while it is immersed in the water bath. Likewise, ultrasound scanning systems such as described in U.S. Pat. No. 4,433,690 to Green et al. and U.S. Pat. No. 4,434,799 to Taenzer, in which the patient's tissue is almost entirely enclosed within the apparatus, offer no capability to perform real-time, image guided biopsy.

Needle guides, which are attached to an ultrasound scanning device, such as described in U.S. Pat. No. 4,058,114 to Soldner, provide aiming of a biopsy needle into tissue using real-time ultrasound images. Such devices, however, constrain the biopsy needle to be in a fixed relation to the ultrasound transducer, may be cumbersome to use, and are not suitable for larger biopsy devices.

U.S. Pat. No. 5,660,185 to Shmulewitz et al. and U.S. Pat. No. 5,664,573 to Shmulewitz describe ultrasound imaging and biopsy systems that have advanced the state of the art by providing the capability to perform real-time, image-guided biopsy of breast tissue. These devices, however, only provide access to the patient's tissue either through the space between the upper and lower compression plates, or through a grid-style compression plate.

In view of the foregoing, it would be desirable to provide ultrasound scanning and biopsy apparatus that permits increased access to the patient's tissue to perform real-time, image-guided biopsy compared to previously known systems.

A further drawback of previously known devices is that steps must be taken to sterilize and clean the equipment after each biopsy. Accordingly, it further would be desirable to provide ultrasound scanning systems that employ disposable components, so that portions of the system that contact patient's blood during an examination may be readily sterilized or discarded.

SUMMARY

In view of the foregoing, it is an object of the present disclosure to provide ultrasound scanning and biopsy apparatus that permits increased access to the patient's tissue to perform real-time, image-guided biopsy.

It is a further object of the present disclosure to provide ultrasound scanning systems that employ disposable components, so that portions of the system that contact a patient's blood during an examination may be readily sterilized or discarded.

These and other objects of the present disclosure are accomplished by providing an ultrasound scanning system in which an upper compression member of the system includes a thin, flexible, sterile membrane which compresses the tissue and is performable by a biopsy instrument. In a preferred embodiment, a scanning and biopsy examination stand is provided having a lower compression surface that houses an ultrasound-transducer. The ultrasound transducer provides real-time ultrasound imaging of tissue disposed on the lower compression surface.

In accordance with the present disclosure, the thin, flexible and sterile membrane forms an upper compression member of the system, and is selectively affixed to the lower compression surface by a tensioning system. The membrane is conformable to the patient's anatomy. In addition, a biopsy instrument contact with the exterior surface of the membrane becomes visible in the ultrasound scan generated by the ultrasound transducer. Accordingly, the biopsy instrument may be inserted into the tissue through the membrane at any desired angle, guided by the ultrasound image. Further in accordance with the present disclosure, the membrane comprises a low cost material that may be discarded after a biopsy.

BRIEF DESCRIPTION OF THE DRAWINGS

Further features of the disclosure, its nature and various advantages, will be more apparent from the accompanying drawings and the following detailed description of the preferred embodiments, in which.

DETAILED DESCRIPTION OF THE PREFERRED EMBODIMENTS

Figure 1:
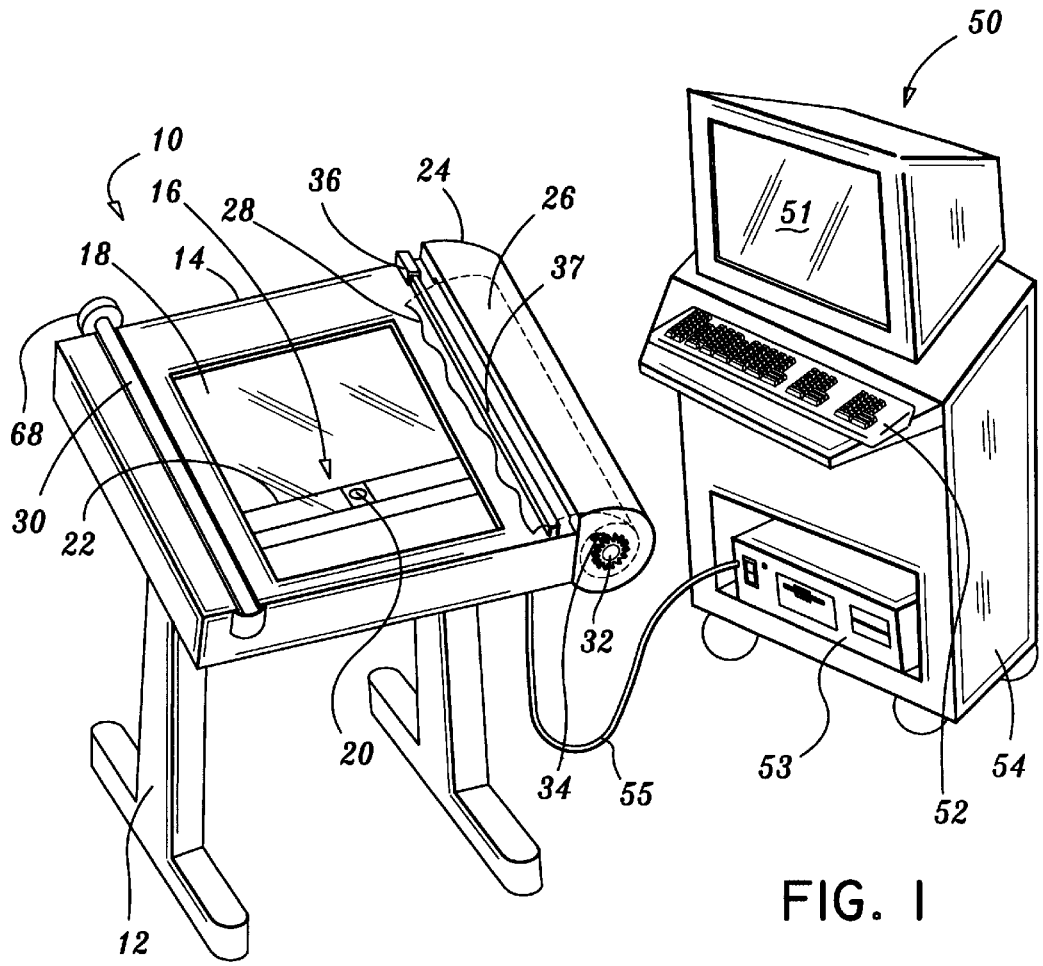
FIG. 1 is a perspective view of apparatus constructed in accordance with the present disclosure.

Referring to FIG. 1, ultrasound scanning and image-guided biopsy system 10 constructed in accordance with the principles of the present disclosure is described. System 10 includes adjustable height base 12 supporting table 14, and work-station 50. Table 14 includes ultrasound scanner 16 disposed beneath, and acoustically coupled to, sonolucent window 18. Ultrasound scanner 16 includes ultrasound transducer 20 mounted on movable gantry 22. Table 14 includes cartridge 24 holding roll 26 of a thin, flexible, conformable and presterilized membrane 28 disposed along one edge, and tensioning bar 30 located on the opposing edge of the table. Cartridge 24 includes gear 32 and lever 34 that lock roll 26 at a selected position within cartridge 24. Cutting element 36 is disposed for sliding movement along rail 37.

Work-station 50 includes monitor 51, keyboard 52 and computer 53 located in cart 54. Computer 53 is preferably an IBM compatible work-station and is programmed to control ultrasound scanner 16 to acquire and display ultrasound images of tissue disposed upon table 14. Work-station 50 is coupled to ultrasound scanner 16 via cable 55.

In accordance with the present disclosure, membrane 28 includes a thin, flexible, presterilized membrane formed, for example, from cloth, paper, plastic (e.g., polyethylene) or combinations thereof. One preferred material for use as membrane 28 is the Steridrape® surgical drape material commonly used in open surgical procedures (Steridrape® is a registered trademark of 3M Surgical Division, 3M Company, St. Paul, Minn.). This material both conforms to the patient's anatomy and may be easily perforated with a biopsy instrument. Other materials may include paper-based or polymer sheets, provided only that the material is sturdy enough to be put in tension without stretching.

Figure 2:
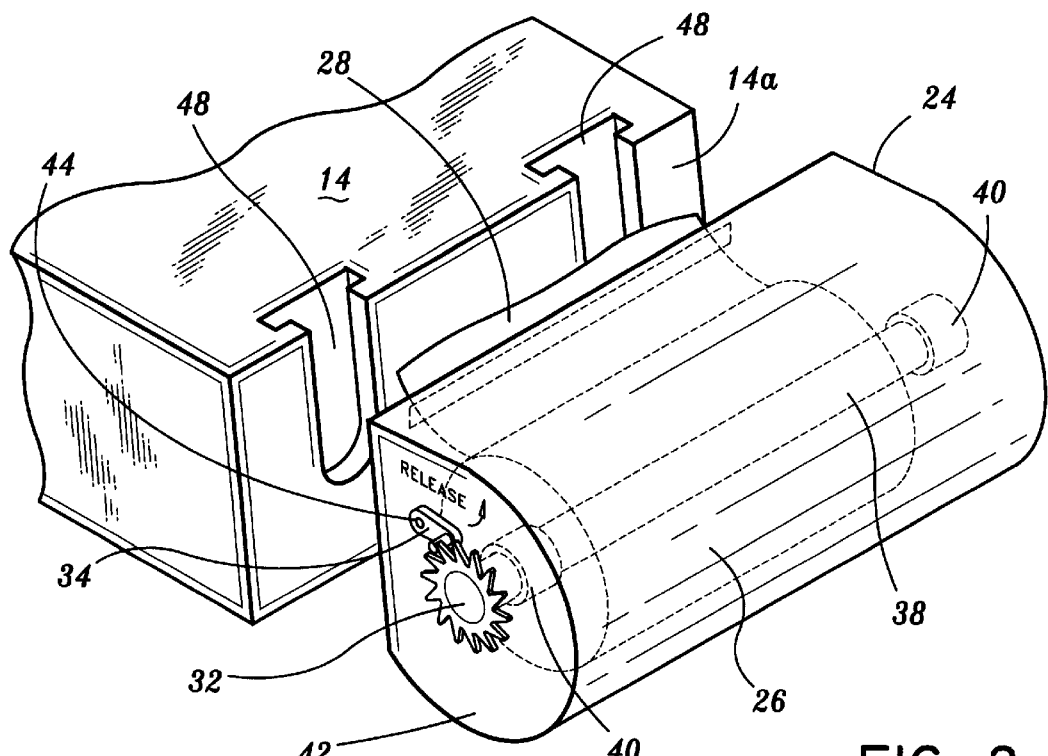
FIG. 2 is a perspective view of the cartridge of a preferred embodiment of the present disclosure.

Referring to FIG. 2, an illustrative embodiment of cartridge 24 containing membrane 28 is described. Membrane 28 is disposed within cartridge 24 on roll 26, thereby enabling a sheet of membrane 28 of desired length to be unrolled from roll 26. Roll 26 is supported to rotate about its longitudinal axis on spindle 38, in turn carried on bushings 40 disposed in the end walls of cartridge 24. One end of spindle 38 projects through end wall 42 of cartridge 24 and carries gear 32. Lever 34 is disposed on the exterior surface of end wall 42, and may be selectively rotated on pin 44 either to permit rotation of gear 32 or to engage and prevent rotation of gear 32. In this manner, lever 34 may be selectively moved by a clinician to permit membrane 28 to be unrolled from roll 26, or lowered into meshing engagement with gear 32 to prevent further rotation of gear 32 and roll 26.

Cartridge 24 includes pins (not shown) that engage slots 48 in lateral face 14*a* of table 14, thus fastening the cartridge to the table. Cartridge 24 preferably includes a lip seal that prevents ingress of dust into the cartridge. As will be apparent from the foregoing description, cartridge 24 forms a self-contained, disposable unit, which may be easily replaced when the stock of membrane 28 on roll 26 is exhausted. Alternatively, membrane 28 may be provided in the form of individual sheets, rather than in roll form.

Figure 3:
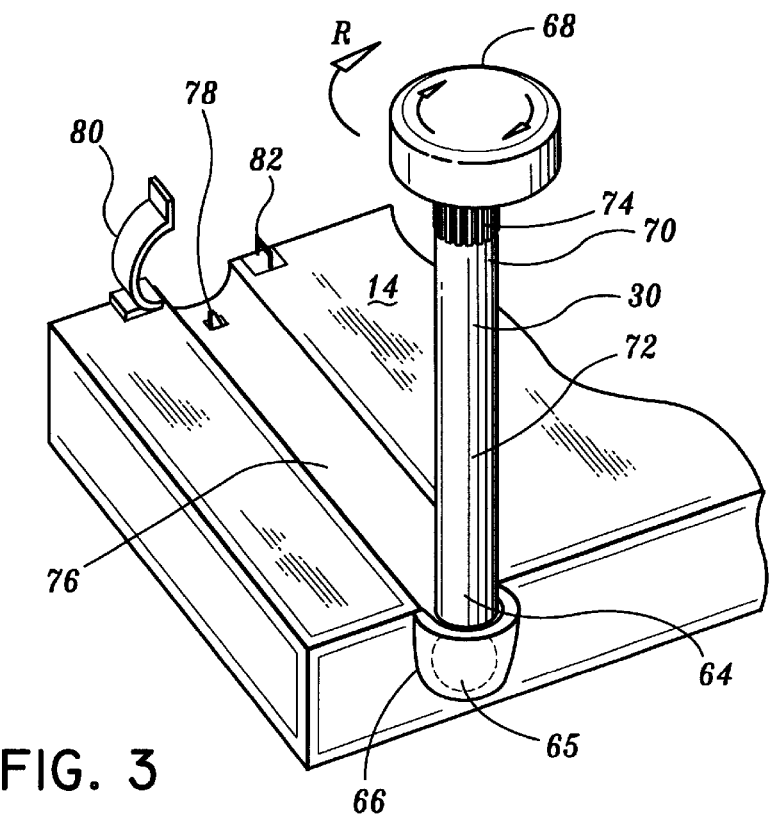
FIG. 3 is an illustrative embodiment of a mechanism for locking a free end of the membrane forming the upper compression surface.

Referring now to FIG. 3, tensioning bar 30 includes end 64 having ball joint 65 engaged in socket 66, and knob 68 disposed on end 70. Tensioning bar 30 preferably made of a rigid material, e.g., stainless steel, and includes elastomeric coating 72 along its length and gear ring 74 located adjacent to knob 68. Tensioning bar 30 has ball joint 65 engaged in socket 66 so that the bar may be moved from a vertical position to a horizontal position wherein the bar is lowered into recess 76 in the upper surface of table 14. Recess 76 includes spring-loaded tooth 78 that engages gear ring 74 of tensioning bar 30 when the bar is lowered into recess 76. Tooth 78 permits tensioning bar 30 to be rotated in one direction, but engages gear ring 74 to prevent rotation in the opposite direction, thereby providing a ratcheting effect.

Table 14 includes buckle 80 near the edge of the table opposite to socket 66. When tensioning bar 30 is lowered to its horizontal position in recess 76, buckle 80 is closed over the top of tensioning bar 30 and fastened into place by clip 82. Buckle 80 exerts a clamping force on tensioning bar 30 that causes the elastomeric coating of the tensioning bar to be compressed against the surface of recess 76, while gear ring 74 is held against tooth 78. This compressive load is sufficiently low, however, to enable tensioning bar 30 to be rotated in recess 76 in the direction shown by arrow R. During such rotation, tooth 78 slips over the teeth in gear ring 74 in a ratcheting manner, and prevents rotation of the tensioning bar in the opposite direction.

Table 14 preferably includes a sturdy material, e.g., plastic or metal alloy capable of supporting the components described above and the weight of the patient's tissue. Window 18 forms a first compression surface of the system, and includes a high performance acoustically transparent ("sonolucent") sheet which is sufficiently rigid to support the patient's tissue at a thickness of about 25 micron (1 mil). Window 18 preferably has sufficient rigidity so that the local slope of the plate, under load, does not exceed one degree from the horizontal.

Window 18 may be formed of a polyamide material, such as Kapton®, a registered trademark of E.I. Du Pont de Nemours and Company, Wilmington, Del., Surlyn® ionomers, such as Surly® 8940, available from E.I. Du Pont de Nemours and Company, Wilmington, Del., or a polymethyl pentene, such as TPX® MX-002 and MX-004, available from Mitsui & Co., Tokyo, Japan. Of these materials, the polymethyl pentenes, and TPX® in particular, are preferred due to their lower acoustic attenuation and impedance and higher strength.

Ultrasound transducer 20 preferably includes a single piston, annular or phased array imaging device constructed in accordance with known technology. Such devices permit beam-focussing of ultrasonic energy to provide high resolution images of the internal structures of a patient's tissue. Ultrasound transducer 20 combines both transmit and receive functions that are switched, respectively, between transmitting and receiving operational modes at selected times by computer 53.

Because the internal structure and operation of ultrasonic apparatus is per se known, the specific internal configuration of that apparatus forms no part of the present disclosure. Transducer 20 preferably operates in a range of about 2 to 15 MHz. More preferably, the signal produced by the transducer in the transmit mode is a 10 MHz burst having a 100 dB bandwidth. To improve the transfer of acoustic energy, transducer 20 may in addition be acoustically coupled to the lower surface of window 18 using an appropriate coupling agent such as, for example, glycerol.

Figure 4:
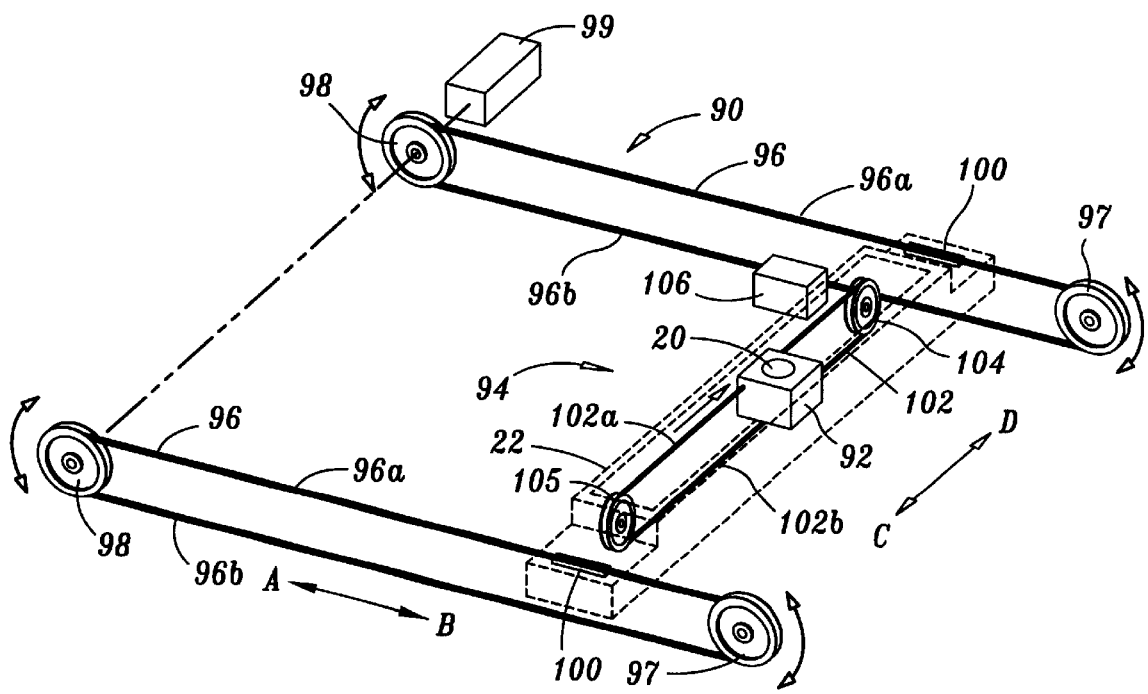
FIG. 4 is an illustrative embodiment of an ultrasound scanning subsystem suitable for use in the apparatus of the present disclosure.

Referring now to FIG. 4, drive system 90 of ultrasound scanner 16 is described. Gantry 22 (shown by dotted lines in FIG. 4) is moved by drive system 90 in directions A and 15 within table 14, and in turn includes carriage 92 that supports ultrasonic transducer 20. Gantry 22 includes its own motorized gantry drive assembly 94 for moving carriage 92 laterally in directions C and D.

In FIG. 4, drive system 90 illustratively includes cables 96 that extend along the lateral sides of table 14. Cables 96 are captured on pulleys 97 and drive wheels 98 to form upper and lower flights 96A and 96B, respectively. Drive wheels 98 are synchronously driven by motor 99. Gantry 22 is fixedly connected to the upper flights of cables 96A at points 100, so that when the upper flights of cables 96 move in directions A, and B, gantry 22 translates in the corresponding direction. Motor 99 is of a type that enables exact positioning of gantry 22, for example, so that the gantry 22 can be moved in the proximal and distal directions in precise increments, such as 1 to 10 mm.

Gantry 22 includes its own cable arrangement 94 for precisely positioning carriage 92 and transducer 20. In particular, in the illustrative embodiment shown, cable 102 runs on drive wheel 104 and pulley 105 to form upper and lower flights 102A and 102B, respectively. Carriage 92 is fixed to upper flight 102A of cable 102 so that carriage 92 moves in directions C and IED in response to movement of upper flight 102A. Motor 106, which is supported on gantry 22, enables precise control of carriage 92 and thus transducer 20.

Alternatively, a toothed belt and gear arrangement may be substituted for the cables, pulleys and drive wheels of the above-described illustrative embodiment. As further alternatives, drive systems 90 and 94 may employ, for example, a motorized track, a threaded block carried on a threaded drive rod (i.e., a lead screw) controlled by an encoder and stepper motor, or any other suitable drive system assembly.

It is to be understood that work-station 50 includes appropriately programmed control circuitry for operating ultrasound scanner 16, for controlling operation of ultrasound transducer 20, and for acquiring, storing, analyzing and displaying data on monitor 51. Illustrative circuitry for operating ultrasound scanner 16 and for analyzing and displaying real-time ultrasound images of tissue disposed on table 14 is described in connection with FIGS. 13 and 14 of U.S. Pat. No. 5,664,573, which is incorporated herein by reference.

Figure 5:
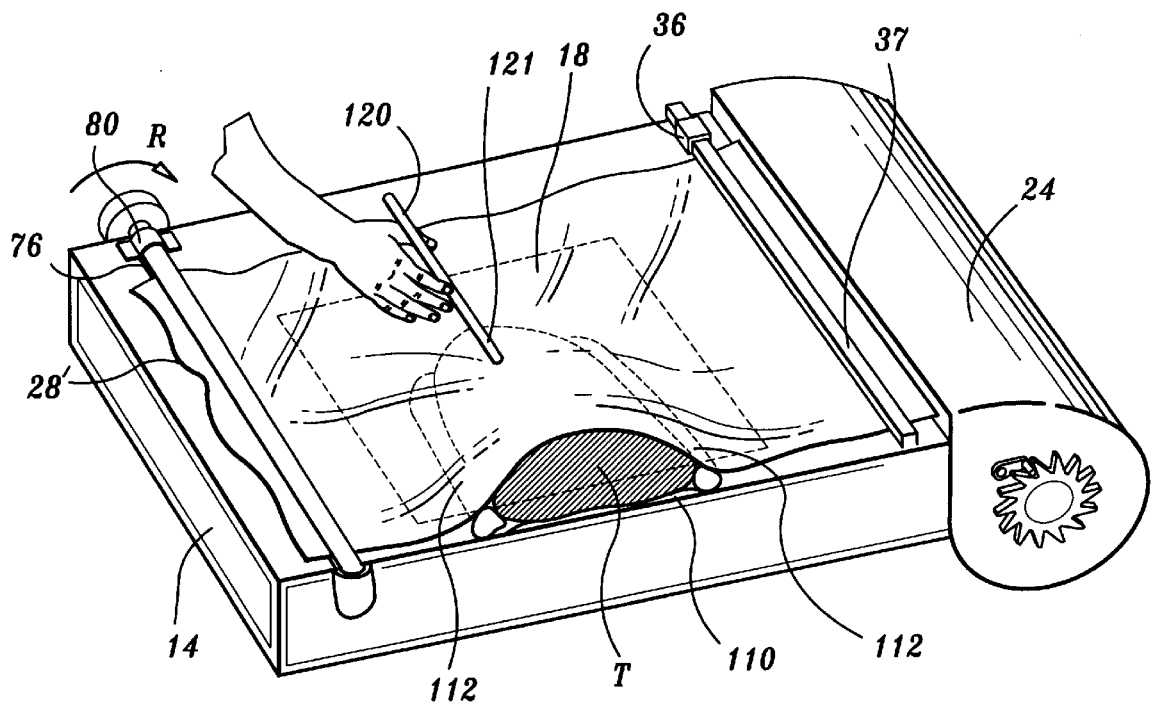
FIG. 5 is a perspective view illustrating use of a biopsy instrument with the apparatus of the present disclosure.

Referring now to FIG. 5, use of system 10 in accordance with the methods of the present disclosure is described. Tissue T to be examined or biopsied, or both, is first disposed on window 18 of table 14. Thin gel pad 110 may be interposed between window 18 and the tissue to improve acoustic coupling therebetween. Additionally, water or gel filled bags 112 optionally may be placed on around the sides of tissue 1 to improve acoustic coupling of the edges of the tissue to the ultrasound transducer.

Once tissue T is disposed on window 18, lever 34 is moved out of engagement with gear 32, and a length of membrane 28 is then unrolled from cartridge 24. The unrolled membrane is draped across the tissue, and lever 34 is again moved into engagement with gear 32, locking spindle 38 from permitting further material to be unrolled from roll 26. Free edge 28' of membrane 28 is then disposed across recess 76 (with tensioning bar 30 in the vertical position). Tensioning bar 30 is then lowered into contact with membrane 28, and forces it into recess 76. Buckle 80 is then fastened across tensioning bar 30, so that gear ring 74 contacts spring-loaded tooth 78.

The clinician then turns knob 68 to rotate tensioning bar 30 in recess 76 in direction R, causing the elastomeric coating 72 to engage membrane 28 and pull it taut across the upper surface of tissue T. Tooth 78 ratchets along gear ring 74 during rotation of tensioning bar 30, and then engages the gear ring to prevent rotation of the tensioning bar in the opposite direction. Upon completion of this step, the tissue is compressed and immobilized against window 18 of the table.

Figure 6:
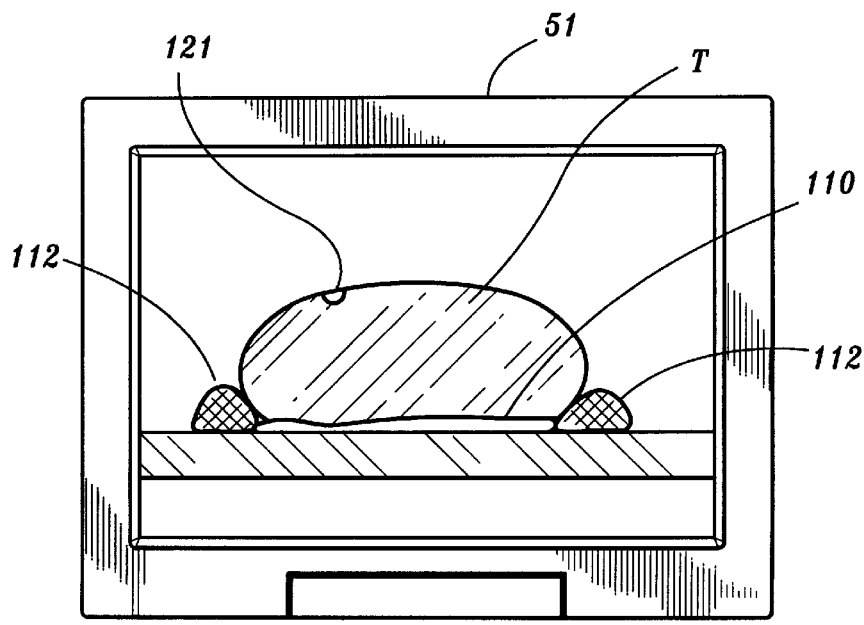
FIG. 6 is a view of a monitor display showing a real-time tissue image and the location of the tip of a biopsy instrument.

Next, ultrasound scanner 16 is activated to generate an ultrasound image of the internal structure of the tissue, which is displayed on monitor 51 of work-station 50, as shown in FIG. 6. In accordance with the present disclosure, the clinician may place tip 121 of biopsy instrument 120 (illustratively, a biopsy needle in FIG. 6) against the upper surface of membrane 28. Using keyboard commands entered at work-station 50, the clinician then adjusts the location of gantry 22 to align the ultrasound image with the biopsy instrument, thereby making the tip of the biopsy needle visible in the ultrasound image (see FIG. 6). Alternatively, the gantry may be left at a desired location and tip 121 of biopsy instrument 120 repositioned until it appears in the image displayed on monitor 51.

Once the biopsy instrument is aligned with a suspected lesion in the ultrasound image, the clinician urges the tip of the biopsy instrument to pierce the membrane and enter the tissue. The biopsy instrument is then manipulated, guided by real-time images of the needle inserted within the tissue, to perform the biopsy. Accordingly, the clinician may perform a biopsy with a high degree of confidence that material extracted using the biopsy instrument in fact came from a desired region of tissue.

In accordance with the principles of the present disclosure, the clinician may freely puncture membrane 28 to biopsy a portion of the tissue, without interference from a rigid upper compression plate, such as are present in previously known devices. In addition, when the biopsy has been completed and the tissue removed, cutting device 36 is moved along rail 37 to sever the soiled length of membrane, thereby permitting it to be discarded along with gel pad 110 and gel filled bags 112.

Figure 7:
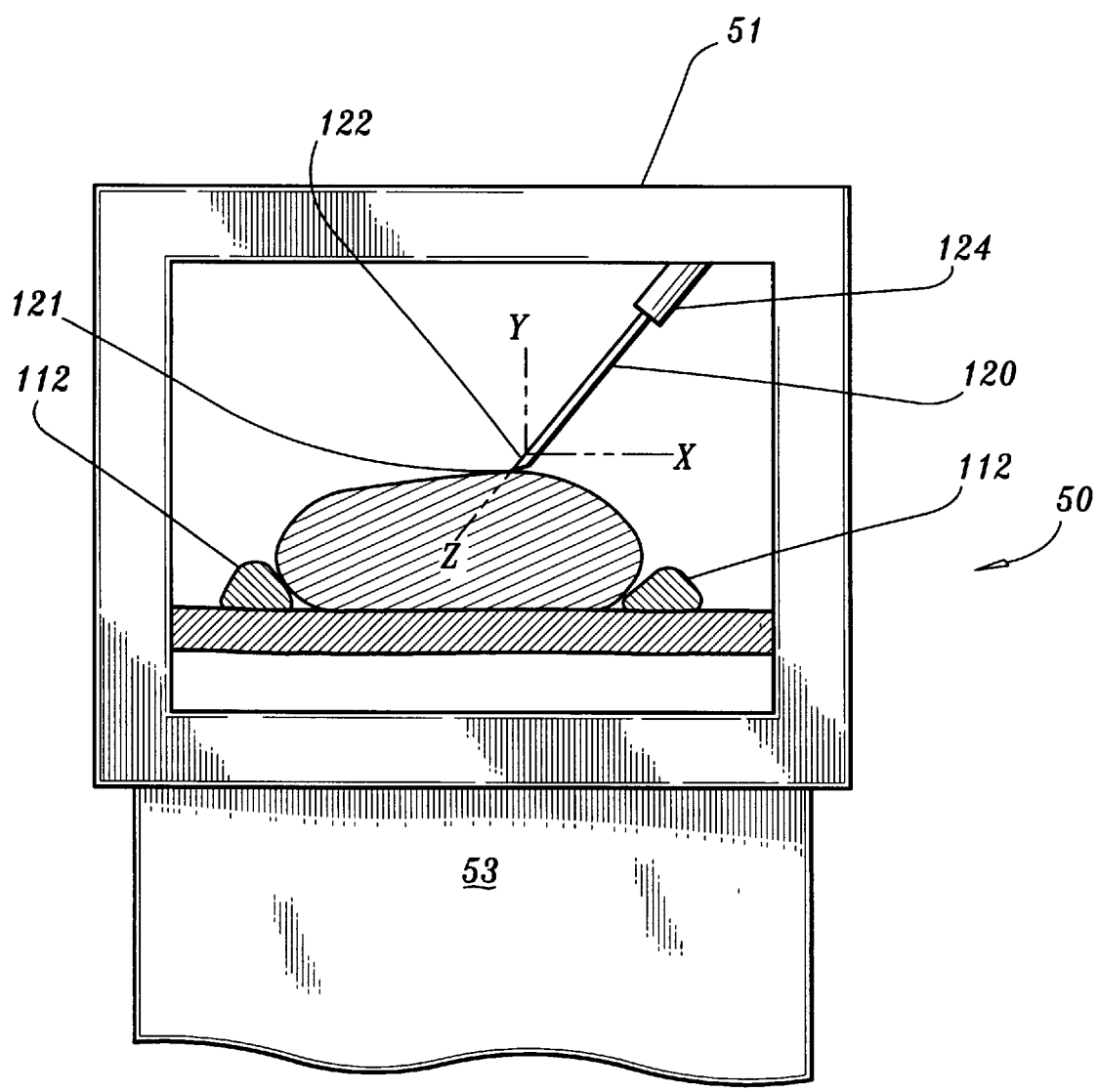
FIG. 7 is an illustrative view of an alternative embodiment of a biopsy instrument with the apparatus of the present disclosure.

With reference to FIG. 7, alternative structure can be provided for mechanical alignment and advancement of the biopsy instrument 120. Such structure can include, for example, an articulated arm 124 that supports the biopsy instrument 120 and that has a three-dimensional position indicator 122 that relates to the distal tip 121 of the biopsy instrument 120. Spacial alignment along the position indicator (X-Y-Z axes) of biopsy instrument 120 can be viewed through display monitor 51. Additionally, as discussed in previous embodiments, X-Y-Z axes coordinates may be entered into computer 53 of work station 50 to advance and align biopsy instrument 120 to the desired sight.

As will be apparent to one of skill in the relevant arts, the present disclosure provides an upper compression surface for use in ultrasound imaging systems that permits a wide range of access to the patient's tissue to perform a biopsy. As an alternative to, or in addition to, the method described hereinabove for localizing the tip of a biopsy instrument, biopsy support apparatus such as described in commonly assigned U.S. Pat. No. 5,660,185, incorporated herein by reference, also may be advantageously used with the apparatus of the present disclosure.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. Apparatus for securing biological tissue to an ultrasound scanning table having a compression surface, the ultrasound scanning table generating ultrasound images of the tissue, the apparatus comprising:
   a membrane that is conformable and performable; and
   a locking mechanism for engaging the thin, flexible, presterilized membrane to the compression surface to compress and immobilize the tissue between the membrane and the compression surface.

2. The apparatus as defined in claim 1, wherein the locking mechanism for engaging comprises:

a tensioning bar; and rotating assembly for rotating the tensioning bar to pull the membrane taut.

3. The apparatus as defined in claim 1, wherein the locking mechanism for engaging further comprises:

a roll of the membrane affixed to a spindle; and a ratchet mechanism coupled to the spindle to control unrolling of the membrane from the roll.

4. The apparatus as defined in claim 3, wherein the roll is presterilized and is housed within a replaceable cartridge.

5. The apparatus as defined in claim 1, wherein the ultrasound scanning table further comprises a cutting device for severing a soiled portion of the membrane.

6. The apparatus as defined in claim 2, wherein the rotating assembly further comprises:

a recess formed in a surface of the ultrasound scanning table;

a ball joint disposed on a first end of the tensioning bar, the ball joint arranged to permit the tensioning bar to be selectively moved from a vertical position to a horizontal position;

a buckle that clamps the tensioning bar in the horizontal position; and a knob coupled to a second end of the tensioning bar.

7. The apparatus as defined in claim 6 further comprising a ratcheting mechanism that permits rotation of the tensioning bar, while in the horizontal position, only in a direction that tautens the membrane.

8. The apparatus for performing a biopsy of biological tissue guided by real-time ultrasound images, the apparatus comprising:

a sonolucent compression surface against which the biological tissue is secured;

a membrane that is conformable and performable;

a locking mechanism for engaging the membrane to the compression surface to compress and immobilize the tissue between the membrane and the compression surface;

an ultrasonic transducer disposed adjacent to, and acoustically coupled to, the compression surface; and a work-station that controls activation of the ultrasonic transducer to generate and display ultrasound images of the biological tissue.

9. The apparatus as defined in claim 8, further comprising a drive system for moving the ultrasonic transducer to generate ultrasound images of the tissue at a plurality of spaced-apart locations.

10. The apparatus as defined in claim 9, wherein the drive system comprises:

a gantry; and gantry drive assembly for moving the gantry.

11. The apparatus as defined in claim 8, wherein the locking mechanism comprises:

a tensioning bar; and rotating assembly for rotating the tensioning bar to pull the membrane taut.

12. The apparatus as defined in claim 8, wherein the locking mechanism further comprises:

a roll of the membrane affixed to a spindle; and a ratchet mechanism coupled to the spindle to control unrolling of the membrane from the roll.

13. The apparatus as defined in claim 12, wherein the roll is presterilized and is housed within a replaceable cartridge.

14. The apparatus as defined in claim 8, wherein the ultrasound scanning table further comprises a cutting device for severing a soiled portion of the membrane.

15. The apparatus as defined in claim 11, wherein the rotating assembly further comprises:

a recess formed in a surface of the ultrasound scanning table;

a ball joint disposed on a first end of the tensioning bar, the ball joint arranged to permit the tensioning bar to be selectively moved from a vertical position to a horizontal position;

a buckle that clamps the tensioning bar in the horizontal position; and a knob coupled to a second end of the tensioning bar.

16. The apparatus as defined in claim 15 further comprising a ratcheting mechanism that permits rotation of the tensioning bar, while in the horizontal position, only in a direction that tautens the membrane.

17. A method for securing biological tissue to a compression surface for ultrasound imaging and biopsy, the method comprising steps of:

providing apparatus including an ultrasonic imaging table having a compression surface, a thin, flexible, presterilized membrane that is conformable and performable, and locking mechanism for engaging the membrane to the compression surface;

disposing tissue on the compression surface;

placing the membrane over the tissue;

engaging the locking mechanism to pull the membrane taut to compress and immobilize the tissue between the membrane and the compression surface; and activating the ultrasonic imaging table to generate and display an ultrasound image of the tissue.

18. The method as defined in claim 17, further comprising a step of:

contacting a tip of a biopsy instrument to the membrane so that the tip is displayed in the ultrasound image.

19. The method as defined in claim 18, further comprising a step of:

piercing the membrane with the tip of the biopsy instrument; and manipulating the biopsy instrument within the tissue while guided by the ultrasound image.

20. The apparatus as defined in claim 19, further comprising, upon completion of the biopsy and removal of the tissue, a step of:

severing and discarding a soiled portion of the membrane.

* * * * *